(12) United States Patent
Raspaldo et al.

(10) Patent No.: US 6,379,298 B2
(45) Date of Patent: Apr. 30, 2002

(54) MEDICAL DISSECTION SPATULA HAVING SPREADABLE SPATULA JAW PARTS

(75) Inventors: Hervé Raspaldo, Cannes (FR); Klaus M. Irion, Liptingen; Horst Dittrich, Immendingen, both of (DE)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 09/794,554

(22) Filed: Feb. 27, 2001

Related U.S. Application Data

(63) Continuation of application No. 09/382,093, filed on Aug. 24, 1999, now abandoned, which is a continuation of application No. PCT/EP98/01064, filed on Feb. 25, 1998.

(30) Foreign Application Priority Data

Feb. 25, 1997 (DE) .......................................... 197 07 374

(51) Int. Cl.⁷ ............................................... A61B 17/02
(52) U.S. Cl. ....................................................... 600/219
(58) Field of Search ................................. 600/214, 218, 600/219

(56) References Cited

U.S. PATENT DOCUMENTS 5,403,342 A * 4/1995 Tovex et al. ................. 606/205

FOREIGN PATENT DOCUMENTS

| EP | 0 516 494 | | 4/1992 | |
| FR | 2682278 | * | 4/1993 | ................. 600/219 |

* cited by examiner

Primary Examiner—Paul J. Hirsch
(74) Attorney, Agent, or Firm—St. Onge Steward Johnston & Reens LLC

(57) ABSTRACT

Disclosed is a spatula dissector (10) presenting a body (12) and a flat distal end (14) comprised of two jaw elements (28, 30) capable of spreading relative to the surface of the spatula.

19 Claims, 4 Drawing Sheets

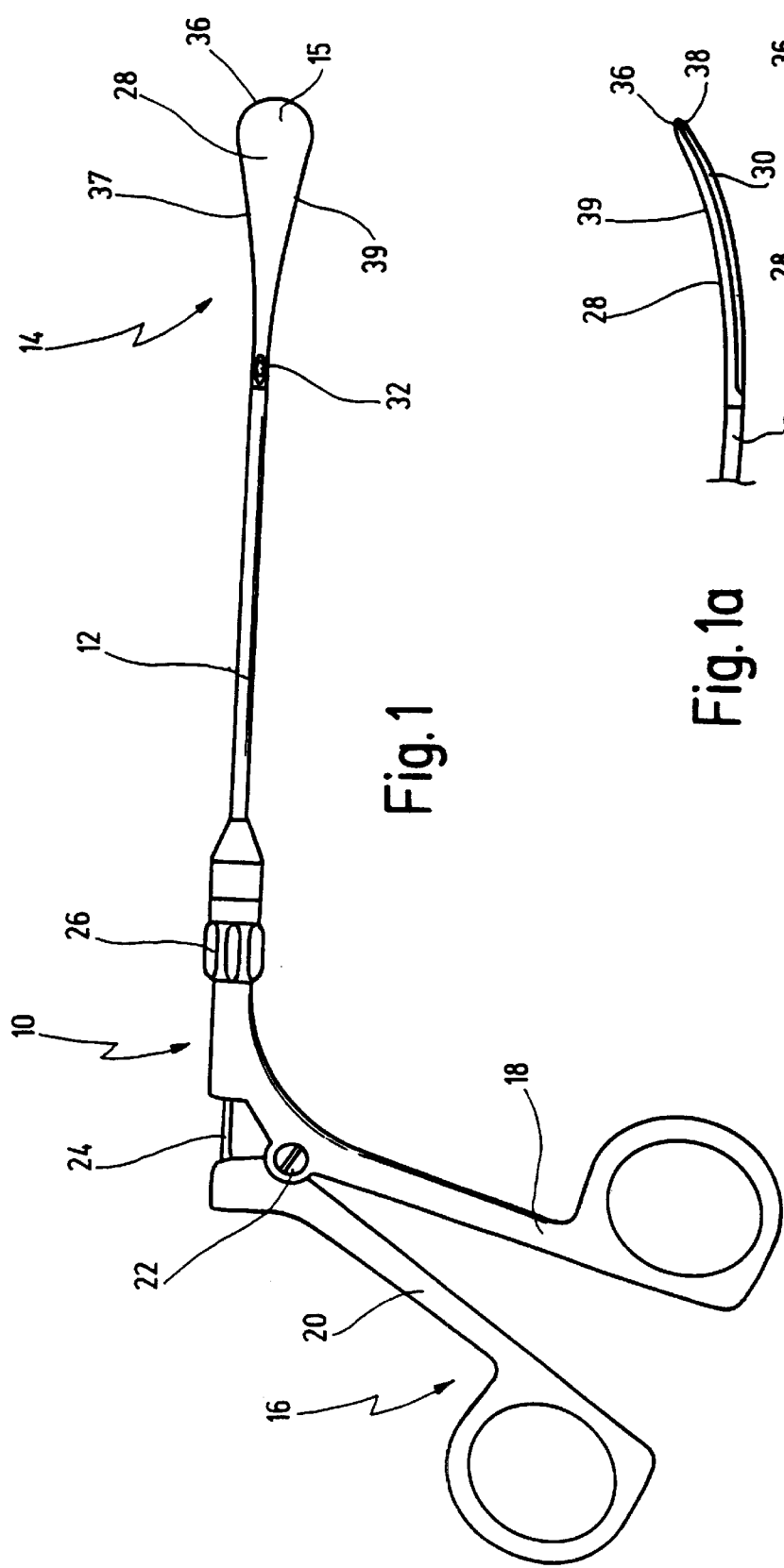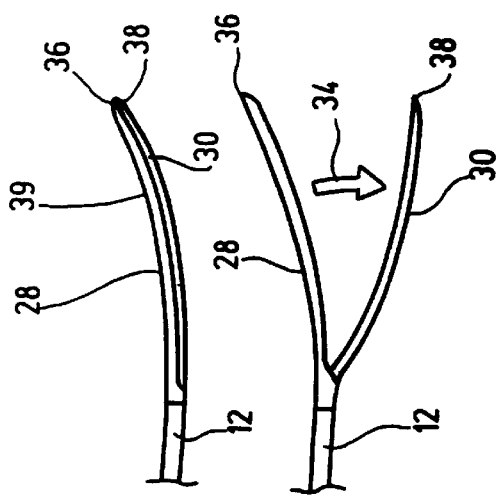
Fig.1
Fig.1a
Fig.1b

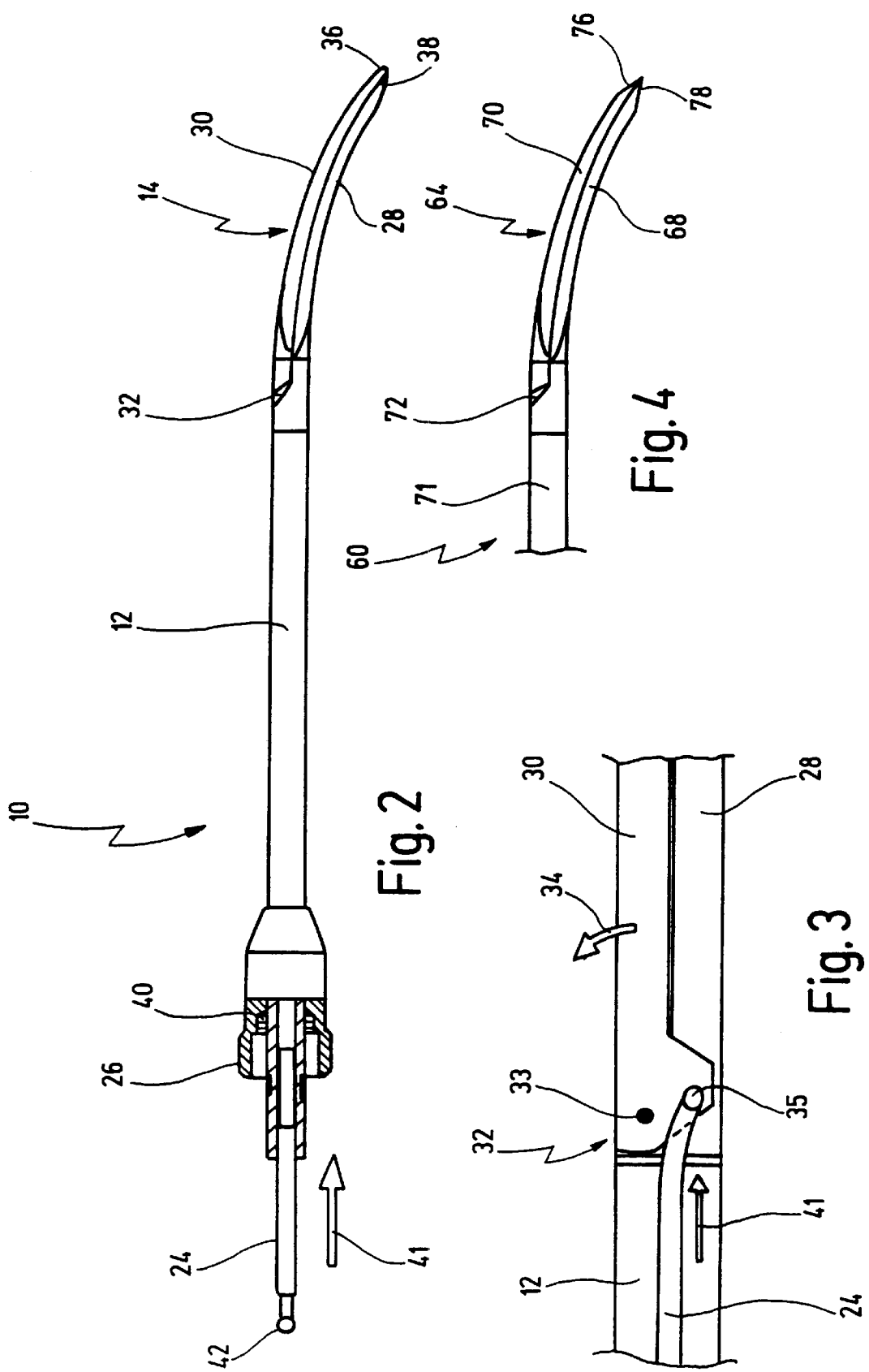

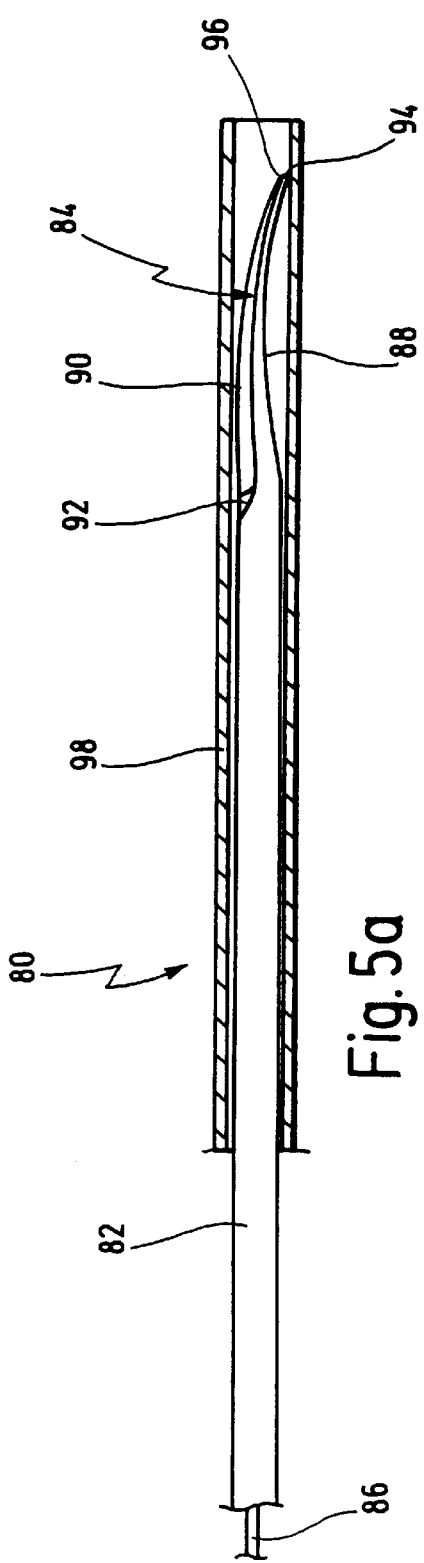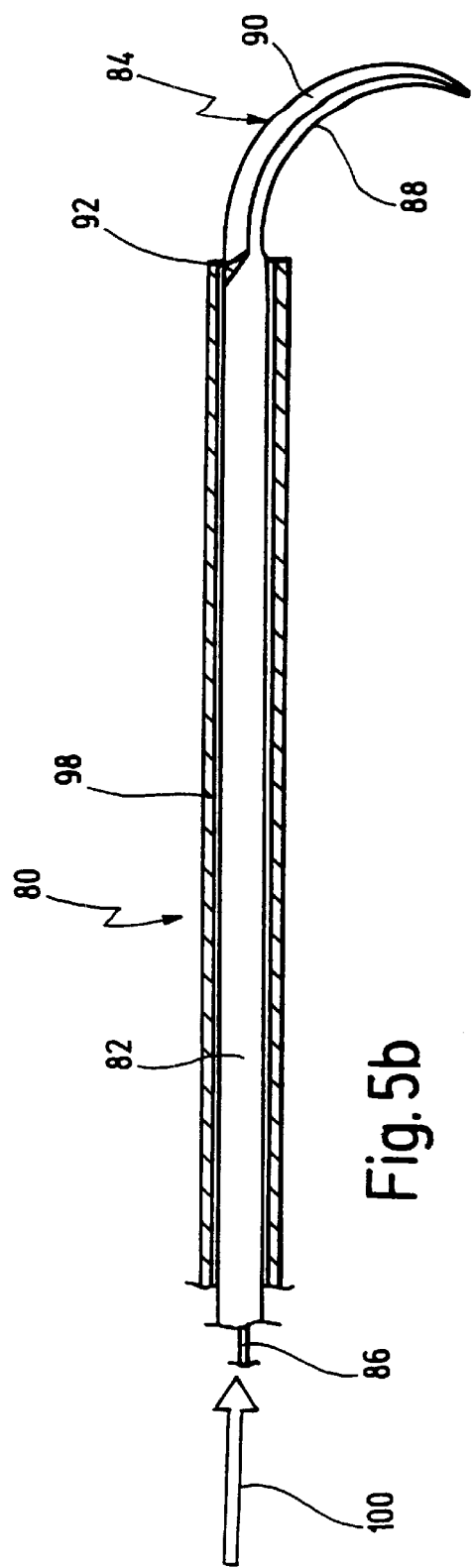

MEDICAL DISSECTION SPATULA HAVING SPREADABLE SPATULA JAW PARTS

CROSS-REFERENCE TO PENDING APPLICATION

This application is a continuation of U.S. patent application Ser. No. 09/382,093 filed on Aug. 24, 1999 now abandoned, which is a continuation of PCT/EP98/01064 filed Feb. 25, 1998.

BACKGROUND OF THE INVENTION

The present invention relates to a medical dissection spatula having a shaft and a distal flat spatula end.

A dissection spatula of this kind is known from the catalog of Karl Storz GmbH & Co. entitled "Storz—Die Welt der Endoskopie" [Storz—the world of endoscopy], 2nd edition, chapter 7, 1/94, page NP 4 A, No. 28176 RE.

Dissection spatulas are used generally in surgery to remove tissue by splitting, cutting, or detaching the tissue from other tissue layers. The distal flat spatula end is used to separate tissue layers from one another, scrape off portions of tissue, or the like. A spatula of this kind can also be used to move a tissue or organ without damaging it.

Dissection spatulas of this kind are used, for example, in cosmetic surgery to detach fatty tissue beneath the skin, for example on the cheeks, in the region of the eyes, or in the region of the nasolabial fold.

The dissection spatula described in the Storz GmbH & Co. catalog under article number 28176 RE is a straight spatula whose shaft transitions into a distal, flattened, blunt spatula end.

To remove an area of tissue, the tissue must be separated from the surrounding tissue by splitting or scraping. This is done by inserting the spatula end between the tissue layers; the spatula is moved laterally back and forth, and the tissue to be removed is gradually detached by lifting the spatula. Only then can the tissue be scraped off or cut up.

Lifting and scraping is problematic with the straight dissection spatula described in the prior art, since the surrounding tissue must experience as little damage as possible, and the clearance for moving the spatula back and forth is therefore limited. Because of the rigid arrangement of the spatula end and the shaft, however, the entire spatula must be moved in order to effect lifting or scraping.

Against this background, it is the object of the present invention to make available a dissection spatula with which tissue or portions of tissue can be detached, split, or separated efficiently and with as little damage as possible, and with which directed manipulation can be ensured using simple means.

SUMMARY OF THE INVENTION

This object is achieved, by way of a medical dissection spatula of the kind cited initially, in that its spatula end has two spatula jaw parts, the spatula jaw parts being spreadable out away from the spatula surface.

Because of the presence of two spreadable spatula jaw parts, the target tissue can now be efficiently split by first bringing the spatula end, with the two spatula jaw parts in the unspread state, to the desired location. In the closed or unspread state, the dissection spatula operates like the dissection spatula cited initially that has only one spatula part. By simply spreading the spatula jaw parts in a direction away from the spatula surface, the tissue to be separated can then be lifted away from the surrounding tissue. The degree to which the two spatula jaw parts are spread depends on the size and extent of the tissue, so that the dissection spatula according to the invention is usable in many ways. If the dissection spatula is to penetrate even further into the tissue, the spatula jaw parts can be closed again and further regions can be separated by back-and-forth movement, and lifted away and detached from one another by spreading the spatula jaw parts again.

The provision of two spatula jaw parts that are spreadable and thus also closable moreover makes it possible to grasp tissue or, for example, also blood vessels. Body parts such as blood vessels or tendons can thus be displaced in order to gain access to tissue located behind them that is to be detached.

If two tissue layers are to be separated from one another over a large area, this can be accomplished with the spatula according to the present invention by introducing it between the two layers and repeatedly spreading the closed spatula jaw parts, and moving them back and forth, to the particular extent required.

With the dissection spatula according to the present invention, these advantages are achieved, without complex technical mechanisms, simply by the provision of two spreadable spatula jaw parts at the distal spatula end.

In a preferred embodiment of the dissection spatula according to the present invention, the two spatula jaw parts broaden toward their distal end.

The advantage here is that with a relatively broad end region, larger regions of tissue can be detached. When holding tissues or portions of tissue, for example muscles, tendons, or blood vessels, it is advantageous that this tissue can be held more securely and less traumatically with distally broadened spatula jaw parts than with narrow spatula jaw parts, since the holding pressure is distributed over a greater holding surface.

In a further preferred embodiment, the two spatula jaw parts rest congruently on one another in the unspread state.

The advantage of this embodiment is that in the unspread state, the dissection spatula can be used like a conventional spatula that requires little space upon introduction into tissue, but at the target location offers all the advantages resulting from spreading of the spatula jaw parts.

In a further preferred embodiment, the two spatula jaw parts are curved out of the shaft axis. In particular, they are curved out of the shaft axis over their entire length.

The advantage here is that the tissue layers, which are often not arranged in straight lines, can be reached better, and that tissue can be detached by scraping in particularly easy and efficient fashion. In facial operations, for example, the spatula jaw parts that are curved over their entire length can be placed against the curved cheekbones.

In a highly preferred embodiment, the transition between the shaft and the broadened spatula jaw parts is smoothly shaped.

This is particularly advantageous because the risk of injury during movement of the spatula is avoided, and nontraumatic dissection is thus possible.

In a further highly preferred embodiment, one of the two spatula jaw parts is joined immovably to the shaft, and the second spatula jaw part is joined movably to the shaft.

This embodiment makes it possible to work particularly safely with the dissection spatula according to the present invention, since spreading occurs with only one jaw part and thus only in one direction. For example, if two tissues are separated from one another by a soft skin or membrane, as is the case, for example, between connective and fatty tissue or between bone and connective tissue, the dissection spatula can be placed with the stationary spatula jaw part against the membrane that must not be damaged. The tissue that is to be separated from the first one is efficiently detached by spreading the one movable spatula jaw part.

This further facilitates handling for the operator because when the spatula jaw parts are closed, the dissection spatula works like a rigid, nonspreadable spatula, and the rigid spatula jaw part serves as a defined placement and guidance element from which, when necessary, the other spatula jaw part can be spread out. The rigid spatula jaw part remains at a specific point.

In a further preferred embodiment, each spatula jaw part has two blunt lateral edges and one blunt end edge.

It is particularly advantageous in this context that the dissection spatula according to the invention allows non-traumatic manipulation, i.e. in a manner that avoids injury. The fact that the spatula jaw parts have blunt boundaries all around prevents undesirable tearing or cutting of tissue that must be left undamaged.

In a further preferred embodiment, at least one spatula jaw part is equipped with a sharp end edge.

The advantage here is that the dissection spatula according to the present invention can also be used as a surgical knife or a scalpel, so that solid tissue areas can be cut with the respective end edge of the spatula jaw parts. For example, blood vessels can also be cut through, or solid connective tissue membranes can be cut off or cut into.

In a preferred embodiment, the end of the spatula jaw parts is configured with an approximately round profile.

This shape allows smooth penetration into the tissue.

In a further preferred embodiment, the end of the spatula jaw parts is configured with an approximately straight profile.

This embodiment has the advantage that scraping of tissue in the region of tissues with a flat configuration, for example on membranes, can be performed particularly efficiently.

In a highly preferred embodiment, the two spatula jaw parts are spreadable by way of an actuation element.

This has the advantage that in the case of a surgical operation in the human body, it is possible to control the movement of the spatula jaw parts from outside. The actuation element can, for example, be joined to the spatula jaw part via a pivot joint.

In a further preferred embodiment, the actuation element is arranged in the interior of the shaft.

It is advantageous in this context that the actuation element can be mounted in space-saving fashion, and in a manner that avoids additional corners and edges.

In a highly preferred embodiment, the shaft is joined to a handle that has one handle element joined immovably to the shaft and a second handle element joined in articulated fashion to the first handle element and in articulated fashion to the actuation element, the two spatula jaw parts being spreadable by moving the second actuation element.

This embodiment has the advantage that the surgeon on the one hand can securely hold the dissection spatula according to the present invention with two fingers of one hand, and at the same time can initiate spreading of the two spatula jaw parts by moving only one finger. This prevents uncontrolled slippage of the dissection spatula, and at the same time allows simple and easily controllable spreading to the particular desired extent.

In a further embodiment of the invention, the spreading direction of the spatula jaw parts extends approximately perpendicular to the movement plane of the second handle element.

The advantage of this feature is that the operator can advance the closed dissection spatula in one direction, and can move the handle elements relative to one another in the same direction, a harmonious operation that can also be superimposed. The spreading action, oriented approximately perpendicular thereto, effectively detaches the tissue parts from one another and then allows the spatula jaw parts, once closed again, to be advanced further. For example, in the performance of a facial operation in which the spatula jaw parts are advanced along the cheekbone toward the eye socket, the surgeon can gradually work forward, from outside via an incision, along the cheek toward the eye socket by advancing the dissection spatula and moving the handle elements in the same direction or in the opposite direction, and by spreading the spatula jaw parts can gradually detach, perpendicular to the advancement direction, those portions of tissue that are to be removed.

In a further embodiment of the dissection spatula according to the present invention, the entire spatula is arranged displaceably within a straight tubular shaft element, the inside diameter of the tubular shaft element corresponding approximately to the width of the two spatula jaw parts.

The tubular shaft element can be configured, for example, as a trocar.

With this embodiment, it becomes possible to use the dissection spatula according to the present invention in minimally invasive surgery as well, so that not only can the spatula be used in the dissection of superficial tissues, but access can also be gained, by introduction through a trocar, to organs or tissues located more deeply.

In a preferred variant of this embodiment, the two spatula jaw parts of the dissection spatula are configured in such a way that upon emerging from the tubular shaft element, they assume a curvature that projects laterally beyond the outer surface line of the tubular shaft element.

In this case the spatula jaw parts can be manufactured from a so-called "memory material" which has the property of reproducibly returning to a specific shape after any deformation. A highly resilient material, such as spring steel, can also be used. For example, the spatula jaw parts are approximately stretched out inside the tubular shaft element so as to fit inside the tubular shaft element, which is as narrow as possible. After being extended out from the tubular shaft element, however, the two spatula jaw parts are curved.

In a further embodiment, the dissection spatula is joined to an endoscope in such a way that the region between the two spatula jaw parts is visible.

The advantage here is that the surgeon can observe his or her manipulations with the spatula end directly, for example, via a monitor, thus making it possible to work in particularly directed fashion with the dissection spatula. An endoscope makes the surgeon's work considerably easier, especially when the dissection spatula according to the present invention is introduced into body parts that are not located superficially.

It is particularly advantageous in this context if the endoscope is movable, in particular is rotatable, relative to the dissection spatula.

In this embodiment, it is possible to view various working areas of the dissection spatula through the endoscope or the endoscopic optical system, and to track, for example, the distal end of the spatula jaw part that is to be spread.

Further advantages are evident from the description below.

It is understood that the features mentioned above and those yet to be explained below can be used not only in the respective combinations indicated, but also in other combinations or in isolation, without leaving the context of the present invention.

BRIEF DESCRIPTION OF THE DRAWINGS

The invention will be explained in more detail below with reference to the drawings, in which:

FIG. 1 shows a side view of a dissection spatula according to the present invention;

FIG. 1a shows a side view, rotated through 90°, of the flat spatula end of the dissection spatula of FIG. 1, specifically in a first operating position in which the spatula jaw parts are closed; and FIG. 1b show a view like that in FIG. 1b, but in a second operating position in which the spatula jaw parts are spaced;

FIG. 2 shows a partially cut-away side view of a portion of a dissection spatula according to the present invention, specifically the shaft, the distal spatula end, and the actuation element;

FIG. 3 shows an enlarged partial representation of the dissection spatula of FIG. 1, in the region of the articulated join between the spreadable spatula jaw part and the actuation element;

FIG. 4 show a further embodiment of the distal spatula end, with a sharp end edge, of a dissection spatula according to the present invention, in a side view;

FIG. 5a shows an embodiment of a dissection spatula according to the present invention in a side view and received in a tubular shaft element, showing a first operating position in which the spatula end lies within the tubular shaft element;

FIG. 5b shows a second operating position in which the distal spatula end is slid out.

DETAILED DESCRIPTION OF PREFERRED EMBODIMENTS

Figure 6:
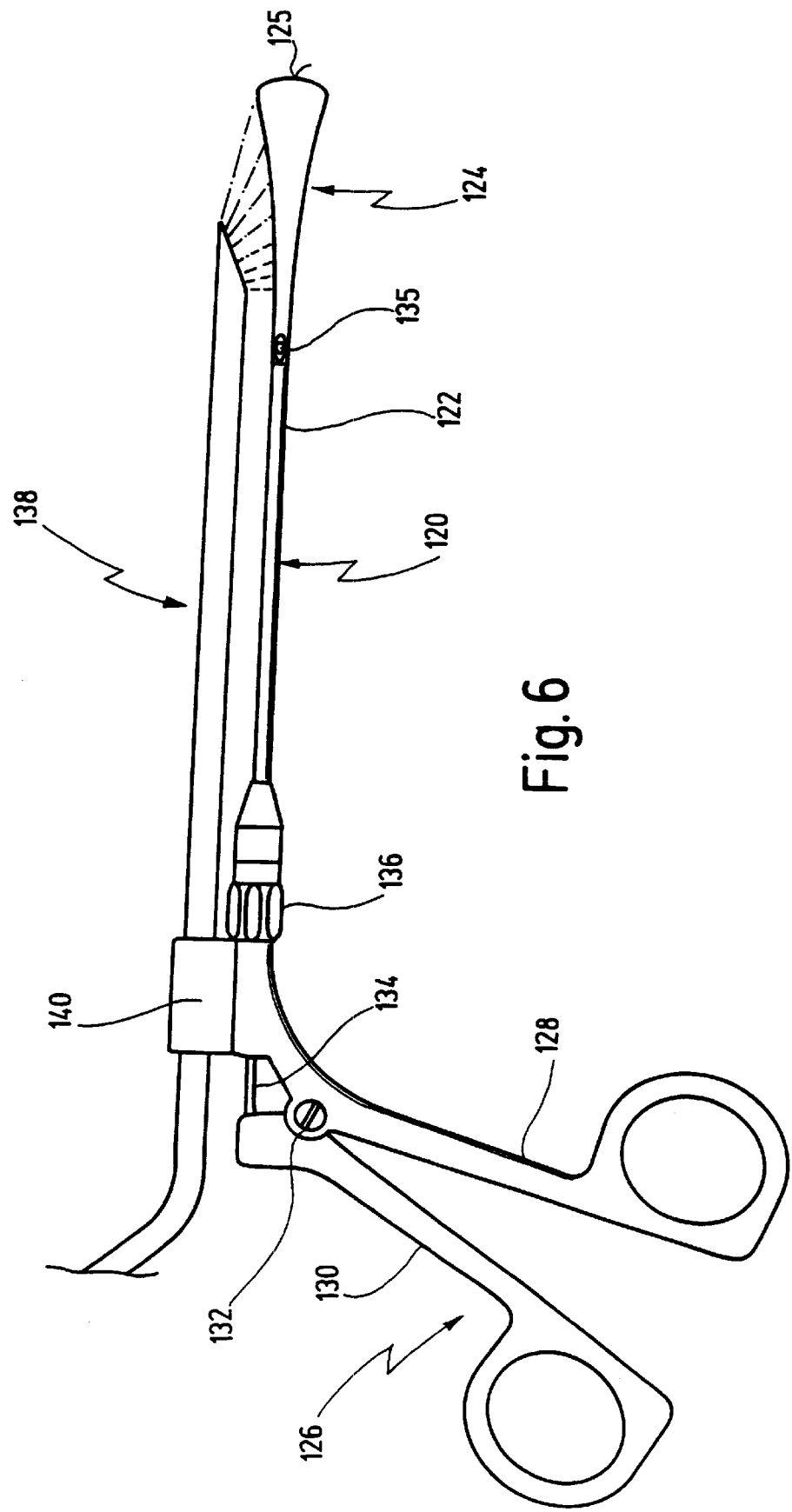
FIG. 6 shows a side view of a further embodiment of the dissection spatula according to the present invention that in this case is joined to an endoscope.

A dissection spatula 10 shown in FIG. 1 has a shaft 12 with a flat distal spatula end 14 whose end 15 is of approximately round configuration. Shaft 12 is joined to a handle 16 that comprises a first handle element 18 joined immovably to shaft 12 and a second handle element 20 that is movable relative to first handle element 18. The two handle elements 18 and 20 of handle 16 are joined via a hinge 22. An actuation element 24 is joined in articulated fashion at its proximal end to movable handle element 20.

Actuation element 24 extends inside shaft 12. Shaft 12, together with the flat distal spatula end 14 and actuation element 24, can be detachably joined to handle 16 via a coupling nut 26. This makes it possible to join handle 16 to different embodiments of the spatula end.

FIG. 1a shows distal spatula end 14 in a side view. In this representation, it is clear that distal spatula end 14 comprises two spatula jaw parts 20 and 30 that are approximately congruent, spatula jaw part 28 being joined immovably to shaft 12 whereas spatula jaw part 30 is pivotable, via a pivot joint 32, relative to spatula jaw part 28 and shaft 12.

In FIG. 1a, the spatula end is depicted in a closed operating position in which spatula jaw parts 28 and 30 rest congruently on one another.

The two spatula jaw parts 28 and 30 resting on one another are curved out of the shaft axis, the transition between shaft 12 and jaw parts 28 and 30 having a smooth profile.

FIG. 1b shows a further operating position of spatula end 14 in which spatula jaw part 30 is spread away from spatula jaw part 28 in the direction of arrow 34.

The two spatula jaw parts 28 and 30 have respective end edges 36 and 38 which are blunt in the embodiment of spatula end 14 depicted in FIG. 1. The respective side edges 37 and 38 are also blunt.

FIG. 2 shows shaft 12, unscrewed from handle 16 and with distal spatula end 14 and actuation element 24, of dissection spatula 10 shown in FIG. 1, in a partially cut-away side view.

Shaft 12 can be thread-joined to handle 18 (FIG. 1) by way of coupling nut 26 equipped with internal threads 40.

It is also evident that actuation element 24 extends in the interior of shaft 12, actuation element 24 being arranged displaceably inside shaft 12.

As is evident from FIG. 3, the two spatula jaw parts 28 and 30 are joined to one another in articulated fashion via a pivot pin 33 which constitutes the pivot axis of the pivotable or spreadable spatula jaw part 30.

At a distance from pivot pin 33, spatula jaw part 30 is joined to actuation element 24 via an eye 35. A linear displacement of actuation element 24 in the direction of an arrow 41 results in pivoting (spreading) of spatula jaw part 30, as indicated by arrow 34. Movement of actuation element 24 in the reverse direction results in closing of spatula jaw parts 28 and 30. Proximally, actuation element 24 has a spherical end 42 that is detachably joined to movable handle element 20 of handle 16 (see FIG. 1), so that pivoting of handle element 20 relative to handle element 18 that is immovably joined to shaft 12 brings about a displacement of actuation element 24 in the distal direction.

FIG. 4 shows a further embodiment of a distal spatula end. Spatula end 64 has two spatula jaw parts 68 and 70 that, in the operating position shown in FIG. 4, rest congruently on one another (unspread state). Spatula jaw part 68 is joined immovably to shaft 71, whereas spatula jaw part 70 is arranged movably via a pivot joint 72. In the embodiment of spatula jaw parts 70 and 68 shown in FIG. 3, the latter have end edges 76 and 78 that are sharp. With a spatula end of this kind it is thus possible to cut through even solid tissue, for example blood vessels or membranes, using the dissection spatula according to the present invention.

FIG. 5a shows a further embodiment of a dissection spatula 80 according to the present invention. A dissection spatula 80 (only partially shown) has a shaft 82 and a distal spatula end 84. Distal spatula end 84 is constructed from one spatula jaw part 88 joined immovably to the shaft and one movable spatula jaw part 90, spatula jaw part 90 being joined via a pivot joint 92 to shaft 82 and to spatula jaw part 88. Movement is accomplished, as described earlier, via a rod-shaped actuation element 86. The end edges 94 and 96 of spatula jaw parts 99 and 90 are blunt. Shaft 82 and spatula end 84 of dissection spatula 80 are placed partially inside a tubular shaft element 98. Tubular element 98 can, for example, be part of a trocar. The inside diameter of tubular shaft element 98 is not substantially greater than the diameter of shaft 82 of dissection spatula 80, and shaft 82 is arranged displaceably inside tubular shaft element 98.

FIG. 5b shows a second operating position of dissection spatula 80, resulting from the fact that shaft 82 has been displaced through tubular shaft element 98 in the direction of an arrow 100 in such a way that distal spatula end 84 projects out of tubular shaft element 98. In this operating position, spatula end 84 has a curvature that projects laterally far beyond the surface line of tubular shaft element 98. The curvature of spatula end 84 comes about because of its material properties, since in this embodiment spatula end 84 is made of a so-called "memory alloy," e.g. a Ni—Ti alloy, which returns to a specific shape after being extended, but is itself once again relatively rigid.

Spatula end 84 of dissection spatula 80 can be displaced back in the direction opposite to arrow 100 by being pulled back into tubular shaft element 98, spatula end 84 once again assuming an approximately stretched-out shape. The operating position assumed is thus once again the one shown in FIG. 4a, and complete withdrawal of dissection spatula 80 from tubular shaft element 98, which is arranged, for example, in the patient's body, can be effected gently and without being impeded by the curvature of spatula jaw parts 88 and 90.

FIG. 6 shows a further embodiment of the dissection spatula according to the present invention. A dissection spatula 120 has a shaft 122 and a distal spatula end 124. End 125 of spatula end 124 is of straight-line configuration in this embodiment. Dissection spatula 120 moreover has a handle 126 that is configured from two handle elements 128 and 130, handle element 128 being joined immovably to shaft 122, whereas handle element 130 is movable, via a pivot joint 132, relative to handle element 128 and shaft 122. In addition, dissection spatula 120 has an actuation element 134 that is joined in articulated fashion to handle element 130 and can be displaced within shaft 122 by moving handle element 130, thus actuating pivot joint 135. Displacement of actuation element 134 once again results in spreading of the spatula jaw parts of spatula end 124.

An endoscope 138 is joined via a mount 140 to dissection spatula 120. Endoscope 138 is not shown in its entirety. Spatula end 124 is visible through endoscope 138, even when the two spatula jaw parts of spatula end 124 are spread. Continuous monitoring of the work being done with the distal spatula end inside the body of a patient is thus possible. Endoscope 138 is movable, so that, for example, the distal end of the spreadable spatula jaw part can be tracked as it is spread.

The embodiment shown in FIGS. 5a and 5b can also be equipped with an endoscopic optical system that is provided on or in the tubular shaft element.

What is claimed is:

1. A medical dissection spatula, comprising
  a shaft, said shaft defining a shaft axis,
  a distal flat spatula end disposed at a distal end of said shaft and having a flat spatula surface,
  said spatula end having two spatula jaw parts, and
  said spatula jaw parts being spreadable out away from said spatula surface between an unspread state and a spread state; where one of said two spatula jaw parts is joined immovable to said shaft, and the second of said two spatula jaw parts is joined movably to said shaft.

2. The dissection spatula of claim 1, wherein said two spatula jaw parts broaden toward their distal end.

3. The dissection spatula of claim 1, wherein said two spatula jaw parts rest congruently on one another in said unspread state.

4. The dissection spatula of claim 1, wherein said two spatula jaw parts are curved out of said shaft axis.

5. The dissection spatula of claim 4, wherein said two spatula jaw parts are curved out of said shaft axis over their entire length.

6. The dissection spatula of claim 1, wherein said two spatula jaw parts broaden toward their distal end, and the transition between said shaft and the broadening spatula jaw parts is smoothly shaped.

7. The dissection spatula of claim 1, wherein each of said two spatula jaw parts has two blunt lateral edges.

8. The dissection spatula of claim 1, wherein each of said two spatula jaw parts has one blunt end edge.

9. The dissection spatula of claim 1, wherein at least one of said two spatula jaw parts is equipped with a sharp end edge.

10. The dissection spatula of claim 7, wherein the distal end of said two spatula jaw parts is configured with an approximately round profile.

11. The dissection spatula of claim 1, wherein each of said two spatula jaw parts has two blunt end edges, and the distal end of said two spatula jaw parts is configured with an approximately straight profile.

12. The dissection spatula of claim 1, wherein said two spatula jaw parts are spreadable by way of an actuation element.

13. The dissection spatula of claim 12, wherein said actuation element is arranged in the interior of said shaft.

14. The dissection spatula of claim 1, wherein said two spatula jaw parts are spreadable by way of an actuation element, and wherein said shaft is joined to a handle that has one handle element joined immovably to the shaft and a second handle element joined in articulated fashion to said first handle element and in articulated fashion to said actuation element, said two spatula jaw parts being spreadable by moving said second handle element.

15. The dissection spatula of claim 14, wherein the spreading direction of said two spatula jaw parts is approximately perpendicular to the movement plane of said second handle element.

16. The dissection spatula of claim 1, wherein it is arranged displaceably within a straight tubular shaft element whose inside diameter corresponds approximately to the width of said two spatula jaw parts.

17. The dissection spatula of claim 16, wherein said two spatula jaw parts are configured in such a way that upon emerging from said tubular shaft element, they assume a curvature that projects laterally beyond the outer surface line of said tubular shaft element.

18. The dissection spatula of claims 1, wherein it is joined to an endoscope in such a way that the region between said two spatula jaw parts is visible.

19. The dissection spatula of claim 18, wherein said endoscope is movable, in particular is rotatable, relative to said dissection spatula.

* * * * *